(12) United States Patent
Keating

(10) Patent No.: US 11,571,154 B2
(45) Date of Patent: Feb. 7, 2023

(54) SPECIAL NEEDS IOT DEVICE AND SYSTEM FOR PARENTS, SCHOOLS AND MEDICAL COLLABORATION

(71) Applicant: Inspired Futures AI, LLC, Enumclaw, WA (US)

(72) Inventor: Nikody Keating, Enumclaw, WA (US)

( * ) Notice: Subject to any disclaimer, the term of this patent is extended or adjusted under 35 U.S.C. 154(b) by 1087 days.

(21) Appl. No.: 16/222,053

(22) Filed: Dec. 17, 2018

(65) Prior Publication Data

US 2019/0388017 A1 Dec. 26, 2019

Related U.S. Application Data

(60) Provisional application No. 62/688,703, filed on Jun. 22, 2018.

(51) Int. Cl.
| | | |
|---|---|---|
| *G09B 19/00* | (2006.01) | |
| *A61B 5/16* | (2006.01) | |
| *G06N 20/00* | (2019.01) | |
| *G16H 20/70* | (2018.01) | |
| *A61B 5/00* | (2006.01) | |

(52) U.S. Cl.
CPC ............ *A61B 5/165* (2013.01); *A61B 5/0002* (2013.01); *G06N 20/00* (2019.01); *G16H 20/70* (2018.01)

(58) Field of Classification Search
None
See application file for complete search history.

(56) References Cited

U.S. PATENT DOCUMENTS

2013/0218239 A1* 8/2013 Grill .................. A61N 1/36189
607/72

* cited by examiner

*Primary Examiner* — James B Hull
(74) *Attorney, Agent, or Firm* — L/O of Alexis J Saenz

(57) ABSTRACT

An IoT device and system improves on prior approaches to tracking and analyzing symptoms and behavior of special needs individuals. The IoT device may include one or more buttons that can be pressed or held for an extended time by the user. Button presses and duration may be registered in a remote computer as being associated to a symptom or behavior. Patterns may be registered based on a sequence of the button presses and duration. Triggered button events may be collected and transmitted to a host server/network for re-transmission to support team members. In some embodiments, a machine learning module may analyze the collected data for patterns and/or deviations of behavior, which may be displayed to team members. In some embodiments, an automatic prognosis may be generated.

3 Claims, 5 Drawing Sheets

SPECIAL NEEDS IOT DEVICE AND SYSTEM FOR PARENTS, SCHOOLS AND MEDICAL COLLABORATION

CROSS-REFERENCE TO RELATED APPLICATIONS

This application claims benefit under 35 U.S.C. § 119(e) of U.S. Provisional application having Ser. No. 62/688,703 filed Jun. 22, 2018, which is hereby incorporated by reference herein in its entirety.

FIELD

The subject disclosure relates to clinical devices, and more particularly, to a special needs Internet of Things (IoT) device and system for parents, schools and medical collaboration.

BACKGROUND

The disclosure below relates to tracking symptoms and behaviors related to special needs children through a system that leverages a specialized IoT button device. In many special needs systems, behavioral tracking for those working with special needs individuals is a requirement and is commonly audited. Traditional approaches use manual pen and paper tracking of symptoms and behavior. This approach is prone to error as many support members cannot be distracted for long periods of time that is associated with filling out paperwork. Some current technology may use an electronic user interface to input behavior data but similar to the manual pen and paper approach, current electronic systems require one to take their attention away from the special needs individual. In another example, there may exist some applications on mobile phones but these may distract the child (since many are drawn to such mobile electronic devices) or a supporting adult more than help the situation.

In addition, while conventional approaches allow one to manually input data (either by paper or digital field), these approaches may still fall short of providing useful information. One has to read through a paper file and compare written notes from page to page to do any meaningful analysis. In addition, the notes do not in and of themselves provide any immediate indication of a behavioral change that requires immediate attention.

In a separate field, prior art IoT buttons exist in the e-commerce space that may trigger a single transaction when pressed. For example, some e-commerce merchants can register a clicked device which is programmed to automatically purchase an item and have it delivered to the device owner. As will be realized, this type of device does little more than trigger a commercial transaction and more than one press of the device may just repeat the same transaction repeatedly and is not germane to embodiments of the invention disclosed below.

Thus, as can been, there exist problems in the current field of technology for special needs behavioral monitoring and prognosis.

SUMMARY

In one aspect of the disclosure, a system for automated behavioral analysis of a special needs individual is disclosed. The system comprises an Internet of Things (IoT) device including, one or more buttons, wherein button press sequences of the one or more buttons are registered in the system to represent a symptom or behavior when pressed in succession or held for an extended time, a temporary memory storage in the IoT device for recording and storing the button press sequences, and a wireless module configured to transmit recorded button press sequences. The system further comprises a host server or cloud-based server network configured to: receive the transmitted recorded button press sequences; operate a processing server configured to analyze the transmitted recorded button press sequences for patterns; analyze the patterns in comparison to stored known behavior of the special needs individual; and generate an automated prognosis of the analyzed pattern based on the comparison to the known stored behavior, wherein the automated prognosis is output into an electronically displayed result.

In another aspect of the disclosure, a system for automated behavioral analysis of a special needs individual is disclosed. The system comprises an Internet of Things (IoT) device including, a microphone, a temporary memory storage in the IoT device for recording and storing verbal cues input through the microphone, and a wireless module configured to transmit the recorded verbal cues as a data packet; and a host server or cloud-based server network. The host server or cloud-based server network may be configured to: receive the transmitted recorded verbal cues; operate a processing server configured to analyze the transmitted recorded verbal cues; transcribe the recorded verbal cues into text or speech data; analyze the recorded verbal cues in comparison to stored known behavior of the special needs individual; generate an automated prognosis of the analyzed recorded verbal cues based on the comparison to the known stored behavior, wherein the automated prognosis is output into an electronically displayed result including the transcribed text or speech data.

In yet another aspect of the disclosure, a method of generating an automatic prognosis of a special needs individual's behavior is disclosed. The method comprises storing in an electronic storage device, a pre-defined set of button press patterns, wherein the button press patterns represent symptoms or behaviors of the special needs individual; registering a button press pattern triggered by a user observing a displayed behavior or displayed symptom by the special needs individual, wherein the registered button press pattern is input into an Internet of Things (IoT) connected device and transmitted from the IoT connected device to a remote computer server; matching the input at the remote computer server to an electronic file folder associated with the special needs individual; adding the registered button press pattern to the electronic file folder; identifying a stored symptom or behavior associated with the registered button press pattern; determining, by the remote computer server, a prognosis associated with the identified stored symptom or behavior; and electronically delivering the prognosis to one or more support team members associated with the special needs individual It is understood that other configurations of the subject technology will become readily apparent to those skilled in the art from the following detailed description, wherein various configurations of the subject technology are shown and described by way of illustration. As will be realized, the subject technology is capable of other and different configurations and its several details are capable of modification in various other respects, all without departing from the scope of the subject technology. Accordingly, the drawings and detailed description are to be regarded as illustrative in nature and not as restrictive.

DETAILED DESCRIPTION

The detailed description set forth below is intended as a description of various configurations of the subject technology and is not intended to represent the only configurations in which the subject technology may be practiced. The appended drawings are incorporated herein and constitute a part of the detailed description. The detailed description includes specific details for the purpose of providing a thorough understanding of the subject technology. However, it will be apparent to those skilled in the art that the subject technology may be practiced without these specific details. Like or similar components are labeled with identical element numbers for ease of understanding.

In general, and referring to the Figures, exemplary embodiments of the subject technology provide a device, a system and process to track symptoms and behaviors related to special needs children by leveraging an IoT device 110. The IoT device 110 may be programmed as a special purpose device so that actions registered by the IoT device 110 are determined to mean pre-defined data used for automated prognoses of special needs behavior. As will be appreciated, aspects of the technology disclosed address shortfalls in the field of special needs monitoring, which employs a number of pieces of technological equipment (for example, location trackers and medical devices). However, the current technology does not adequately support the treatment of a special needs individual's treatment.

Figure 2:
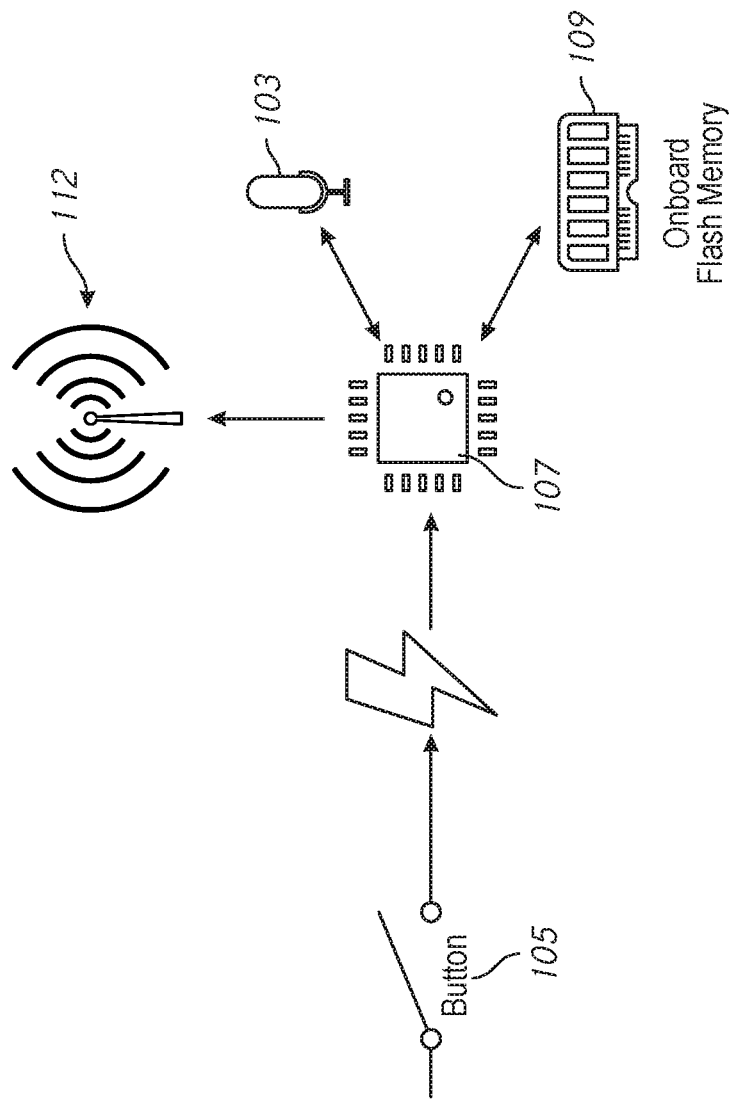
FIG. 2 is a flowchart of a button-based input processing for tracking behavior in accordance with an aspect of the subject technology.
Figure 1:
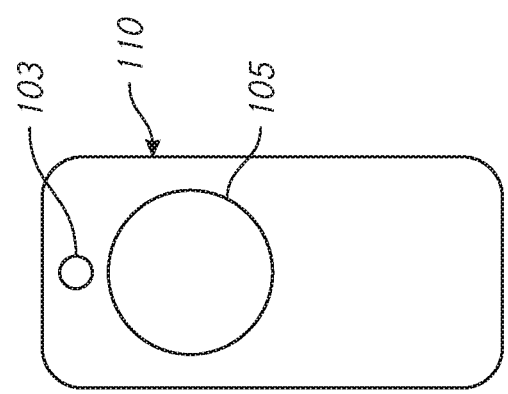
FIG. 1 is a front diagrammatic view of a handheld behavior tracking device in accordance with an aspect of the subject technology.

Referring now to FIGS. 1 and 2, a behavior tracking IoT device 110 (FIG. 1) (sometimes referred to generally as the "device 110" or the "IoT device 110") and a schematic (FIG. 2) for input of a behavior code are shown according to an exemplary embodiment. The device 110 may be handheld and configured for convenient input by either a button being pressed or audio delivery.

The device 110 may include a button 105, which may be a spring type button which may be repeatedly clicked in sequences. A "sequence" as used herein, generally means more than a single press or trigger of the button 105. In some embodiments, the button 105 may be a capacitance-based button which detects taps and holds on the button face by a finger. The sequences registered may include rapid clicks and holds, which in various combinations may be understood by system embodiments to represent various behaviors. The signals registered by the button 105 may be detected by a processor 107 incorporated into the device 110. The processor 107 may be configured to process the button press signals into a format that is readable by system embodiments described below. In some embodiments, the signals detected by the processor 107 may be saved to on-board memory 109. Saved data may include the button press sequences, along with the time and date registered. In addition, the on-board memory 109 may include a device identifier which may be associated with the special needs individual whose behavior or symptoms are being tracked.

Figure 3:
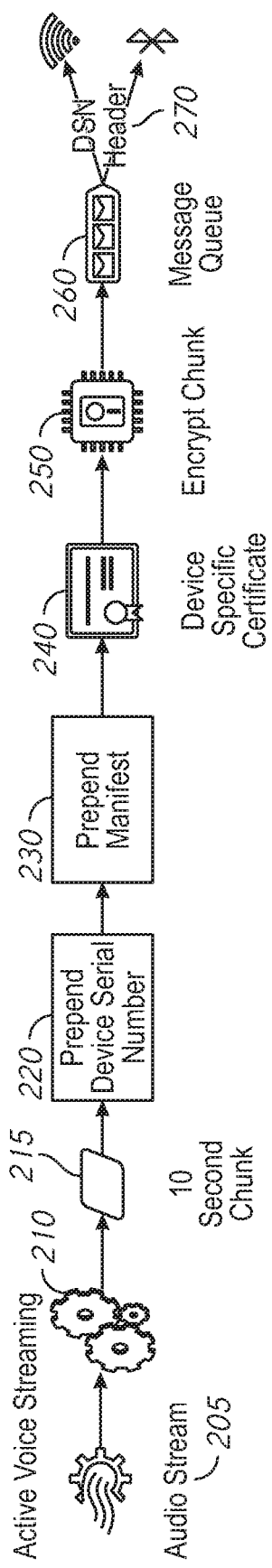
FIG. 3 is a flowchart of a system and process for tracking button presses of an IoT device to track symptoms and behaviors of special needs children in accordance with an aspect of the subject technology.

In some embodiments, the audio input through the microphone 103 may be registered by the processor 107 similar to button presses except that the processor 107 processes audio data under a different format. Audio input commands may include for example, the use of verbal notes and/or code words. In some embodiments, audio input may be transcribed by system embodiments into data which may be evaluated. Referring temporarily to FIG. 3, a process 200 for audio stream processing is shown according to an exemplary embodiment. An audio stream 205, (which may be for example, verbal notes spoken into the microphone 103) may be processed 210 (for example, by the processor 107) as identified as audio data and formatted for behavioral transcription. The process audio data may be parsed into packets (for example, 10 second chunks of audio data). The packets may be prepended 220 with the device identifier serial number. In some embodiments, the packets may also be prepended 230 with a manifest. The manifest may follows the same format as an HTTP live streaming (HLS) manifest file, which contains the name of the sound file along with the duration of the audio file. As new files are created, that file gets appended to in order to easily be able to look up all the files associated with a specific stream. In some embodiments, a security certificate associated with the device 110 may be associated 240 with the audio packet. In an exemplary embodiment, the packet of audio data may be encrypted 250. The encrypted packet may be added 260 into a message queue of signals registered by the device 110. As may be appreciated, an individual's tracked behavior may be sensitive information, and the encryption process protects this information from being accessed by third parties who may be data mining individual's clinical history. In some embodiments providing email notifications, a DSN header may be added 270 to the message so that a notification message indicating new data is available is distributed to recipients associated with the special needs individual's support team.

With either the button press signal or audio recorded signal, the processed packet may be transmitted wirelessly using a transmitter 112 on the device 110.

Figure 4:
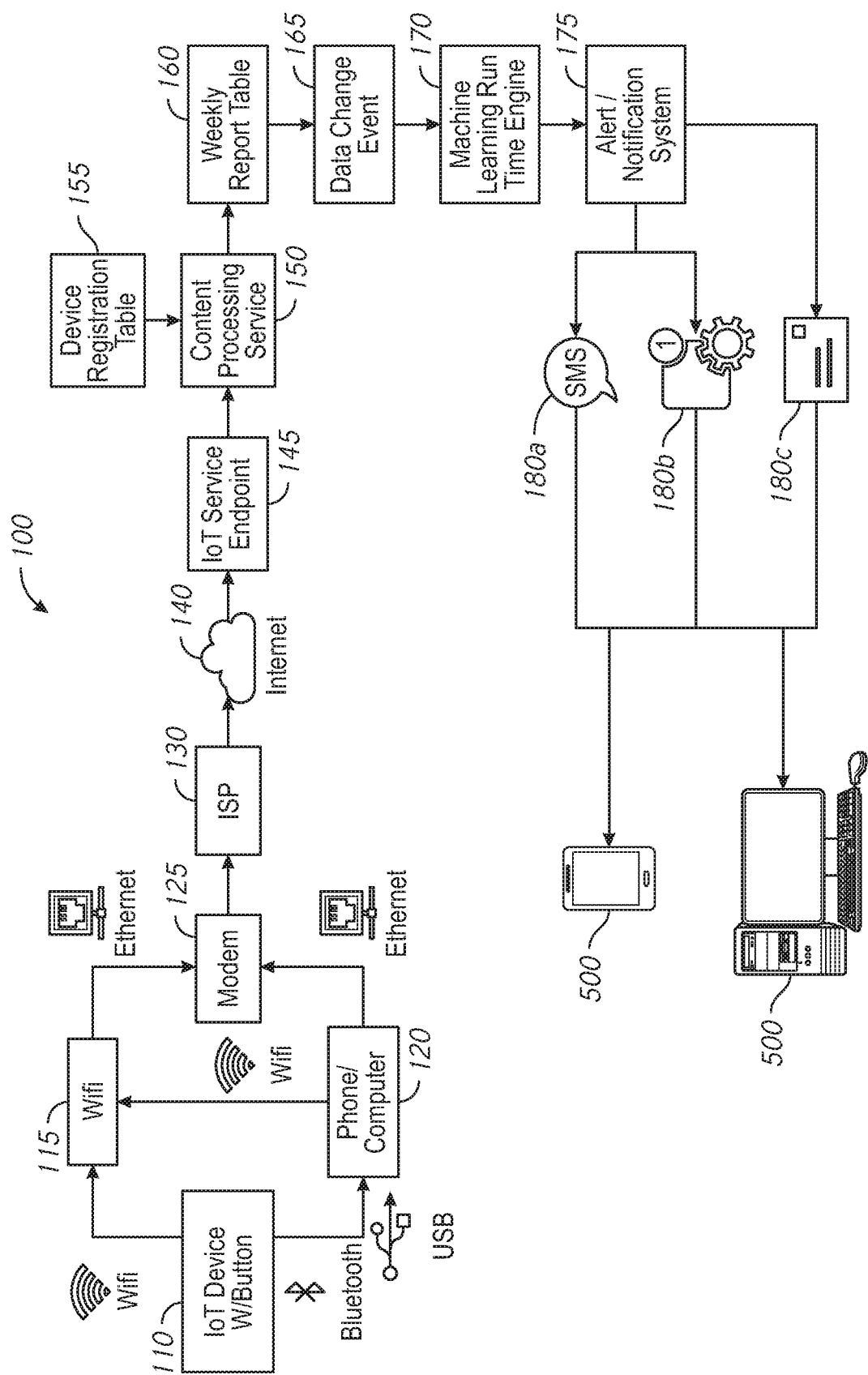
FIG. 4 is a flowchart of a method for processing an audio-based behavior tracking input into an IoT device in accordance with an aspect of the subject technology.

Referring now to FIG. 4, a system 100 for automated special needs prognosis (referred to in general as the "system 100") is shown according to an exemplary embodiment. The system 100 includes the IoT device 110. In an exemplary embodiment, the IoT device 110 may be pre-provisioned with a unique electronic identifier and a security measure may be stored in the device's storage to verify authenticity of the information source (which may include for example, a digital certificate or an encrypted token). Presses or extended holding of the button(s) on the device 110 may be tracked locally (in the device 110) for count and duration and may be either stored locally or transmitted real time to a processing server 150 over encrypted communication to any computer port or IoT endpoint (using a wireless signal from a wireless module in the device including for example, Wi-Fi or short-range protocols). Data from the IoT device 110 may be wirelessly forwarded through for example, a direct WiFi connection 115 (in the device 110) or through a phone/computer 120 when the device 110 is connected to such an intermediary device. Generally, data transmission passes through a modem 125 and on through an internet service provider (ISP) 130 network to the Internet 140. However, some embodiments using a phone 120, may connect to the Internet 140 or the destination by general wireless telephony services. The data may be received at an IoT service endpoint 145, which may comprise for example, one or more computer devices configured to process the data for special needs behavioral prognoses. In some embodiments, the processing server 150 is connected to or a part of, an IoT service endpoint 145. In an exemplary embodiment, users, (including for example members of the support team) may register an IoT device 110 with the system 100. Once registered, behaviors may be mapped to various buttons, combinations of buttons, button press counts, sequences, and durations (which will now be referred to as the "pattern") which may be stored in a device registration table 155. The device registration table 155 may include a file associated with the special needs individual and one or more devices 110 associated with the individual. The device registration table 155 may be stored in the processing server 150 or in a computer/server connected to the server 150. This information is stored on the server side along with the button's unique identifier and a list of patterns defining behaviors of the special needs individual.

When the server 150 receives signals of a pattern, the device's registration is retrieved and the pattern is transformed into behavioral context either through a unique identifier of the behavior or through a known behavior name. In some embodiments, a behavior identifier may be associated with a globally unique identifier (GUID), which may take a format for example of: "56bf473f-1277-497e-bcbd-259ac10e1827". In one embodiment, a known behavior name is supplied by the support team for association with the child. In another embodiment, a universal taxonomy of related symptoms may be stored and referenced in order to support research or general related symptom notifications when the symptoms arise. This information is then stored in a database (for example, in a weekly report table file 160) and an event may be triggered for processing in a detection module 165.

Either after the information is stored or during the process of data ingestion into the system 100, the data may be analyzed leveraging machine learning for changes in trends and in the pattern of behavior or symptom occurrences using a machine learning run time engine 170. Machine learning may be performed through leveraging a machine learning system, to feed information from a pre-set or user selected time frame (for example, the last 5, 90, 182 365, etc. days) of the child's past behaviors. Special needs symptoms and behaviors may be analyzed by the machine learning aspect to quickly identify trends and changes to those trends, allowing for faster identification and communication of changes to the child's support team allowing for more rapid adjustments to the child's support and accommodations plan. As will be appreciated, embodiments using the device 110 may facilitate the process of identifying changes in symptoms or behavior. The device 110 and its use through simple button patterns frees the observer up from taking notes and keeps the observer's focus on the subject individual so that nuances are not missed. The device user's recognition may be tied to the device clicking/pressing as a reflex, which generates more accurate data that can be processed by the system. This may avoid biased or inaccurate note taking by the observer. The machine learning aspect may identify deviations that may be missed by the observer inaccurately assessing the symptoms or behaviors on site.

An example of registering behavior for analysis would include events related to a child irrationally screaming or lashing out. While this might be a common occurrence as the child gets hungry, machine learning according to exemplary embodiments, may differentiate between normal occurrences and abnormal changes based on deviations from historical data, (for example, such as a change in the time of day a behavior occurs such as an uptick in occurrences in the late afternoon). Rather than rely on for example, a conclusion by the support member on site, the system may identify a deviation in the behavior which may trigger an alert (through alert system 175) to the support team. The system may also determine a prognosis based on the identified behavior/symptom based on the environmental context of when the registered behavior/symptom occurred (for example, outputting a needed change in medication administration). When an event is detected, some embodiments may provide an automatic alert or notification to the support team. When reported, the machine learning model which is generated from the data supplied in the timeframe can identify where it identified normal and abnormal occurrences of behaviors. As will be appreciated, this aspect simplifies the analysis by the support team. For example, the process may be used to identify patterns and recognize deviations from those patterns through retrieving a short timeframe in the recent past (for example, the last 5-10 days') worth of information, which may then be evaluated against the machine learning model. In this way the team can be given context as to whether a grouping of data lies outside the area of normal, and can be highlighted for the support team to understand why the machine learning model thought there was a change.

Changes, raw events, and automated prognoses alerts can be subscribed to by the child's support team. This is done through storing these subscriptions in a database. Alerts along with information may be sent to the support team through SMS text systems 180*a*, push notification systems 180*b*, or by email 180*c*. Once the events or changes are identified, the subscription information may then be used to communicate with the child's support team in the method which they have chosen.

Figure 5:
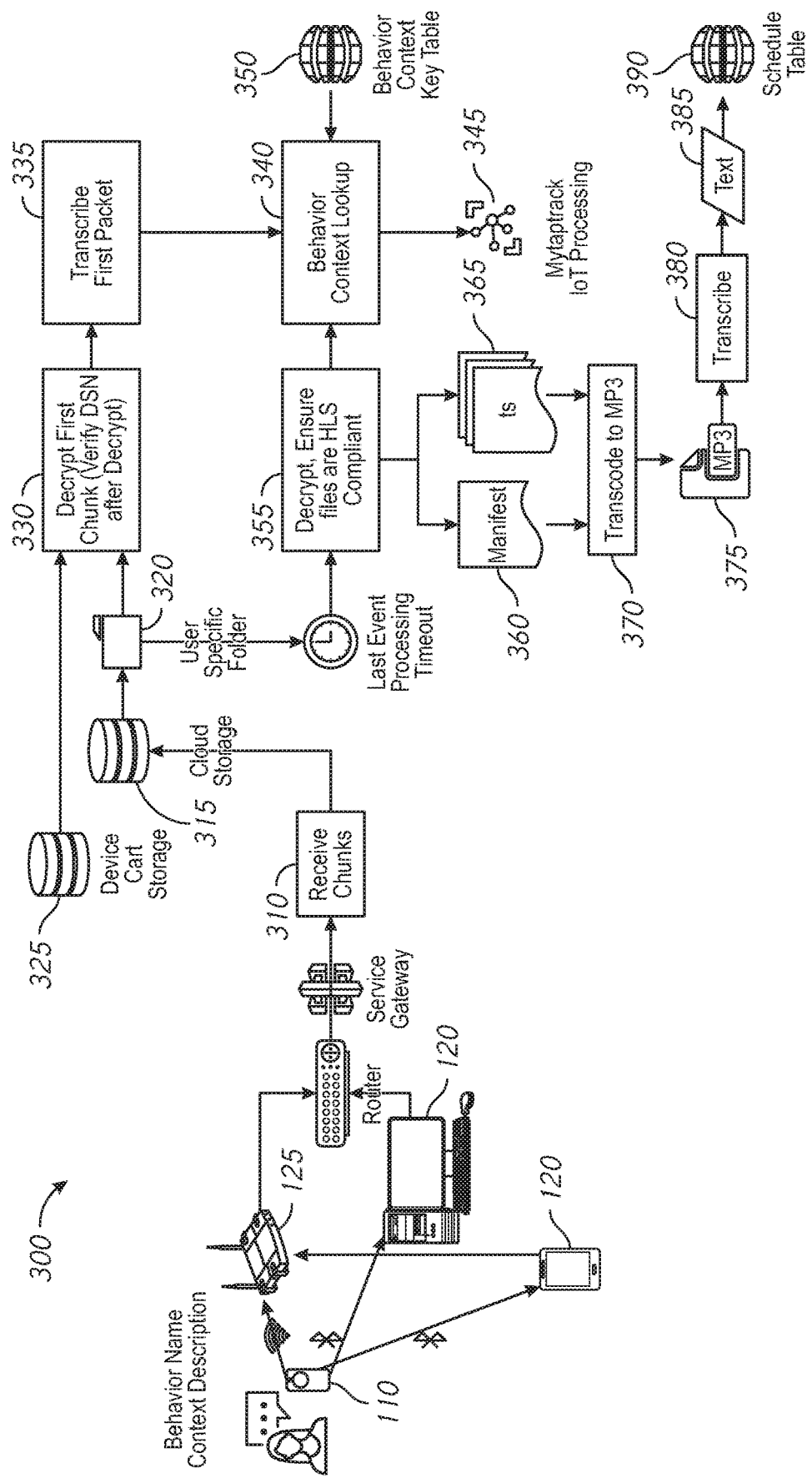
FIG. 5 is a flowchart of a system and process for tracking audio-based input into an IoT device to track symptoms and behaviors of special needs individuals in accordance with an aspect of the subject technology

Referring now to FIG. 5, a system 300 for tracking audio-based input into an IoT device to track symptoms and behaviors of special needs individuals is shown according to an exemplary embodiment. The system 500 may be configured to process verbal cues input into the device 110. The verbal cues may specify a behavior, for example, by using code words or explicit description label of the behavior ("yelled"). The verbal cues may in some embodiments be notes on behavior which just occurred. The verbal notes may be transcribed. The transcriptions may be automatically analyzed by the system 300 to generate findings and in some embodiments, an automated prognosis. The left side of the diagram (to the left of the gateway symbol), represents the input side at the device 110. The pre-processing of audio cues on the left side may operate as described above in FIG. 3 and for sake of brevity, will not be repeated. The right side of the diagram represents processing of the formatted data according to exemplary embodiments.

The elements to the right of the service gateway may in different embodiments, be part of a single computing device 500 (as described in more detail ion FIG. 6) or may be shared between different computing devices 500 (for example, within a network or cloud computing environment). The elements in computing device 500 of FIG. 5 may be electronic modules or sub-processes of a software application. Accordingly, the following description may at times refer to elements as actions rather than as a physical element depending on the context of the element.

As a general step, the computing device 500 may receive 310 chunks of data (for example, as processed packets sent via the wireless communications from the left side of the figure). In some embodiments, the received data may be recorded in storage module 315 (which may be for example, a cloud storage device or database). Once the computing device 500 identifies the source of the data packet, the received data may be saved to a folder 320 associated with the special needs individual. The computing device 500 may identify which folder 320 the data is saved to by analyzing the received data for a device identifier (for example, device serial number 220) and directing the received data to the user folder 320 associated with the device identifier. In some embodiments, the received data may be encrypted. If the data is encrypted, the computing device 500 may reference a certificate database 325 to check whether the certificate information in the received data packet satisfies the criteria in the stored certificate. In response to the security check being satisfied, the computing device 500 may decrypt 330 the received data packet and read the formatted verbal cue data.

In an exemplary embodiment, the computing device 500 transcribes the verbal cue data from its raw format into an audio format. The raw format may be dictated speech. The speech may include for example, spoken observations of the subject using full sentences. In some embodiments, the speech may be for example, verbal shorthand of technical terms. The computing device 500 may identify a number of behavior candidate descriptions from the transcribed data and may reference 340 a behavior context key database 350 to determine what behavior(s) was being recorded by the user. The database 350 may store for example, predefined textual descriptions of the behaviors. The database 350 may also contain a taxonomy of symptom names which are related to be able to associate several terms to a specific behavior/symptom. The database 350 may have information pertaining to symptom/behavior names and the associated identifications for the student. One of the keys would be a list of devices associated with the student, which may be used to retrieve the list of symptoms which to attempt transcription matching against. The transcription matching may then use fuzzy logic, and potentially a taxonomy, to associate the spoken symptom to the list being tracked for the specific student. The transcribed data may be matched to candidates from the predefined textual descriptions. The retrieved candidate behaviors/symptoms may be presented to the support team for evaluation. In some embodiments, as described below, a machine learning process may be applied to the candidate symptoms/behaviors to determine the most likely accurate symptoms or behaviors. In an exemplary, embodiment, the candidate behavior(s) is processed 345 to determine whether any deviation from past behavior exists and generate a prognosis.

In some embodiments, the data received in user folder 320 may be processed into another audio format based on the time needed to convert the raw data received. For example, HTTP live streaming (HLS) protocols may be implemented. If the user records a continual stream and the system needs to write 10-30 seconds worth of data or if the file size exceeds a specific amount such as 50 kb, a processing timeout may be triggered. If the system determines that the incoming data file requires a split, the current file may be ended, and a new file started beginning where the other file left off The new file may be decrypted 355 and checked for HLS compliance. The manifest file may be extracted 360 from the decrypted data. The data programming language files (for example, TypeScript) may be extracted 365 from the decrypted data. In HLS, the MP3 format is used to create small segments of audio, which are given the extension ".ts". These files usually are around 10 seconds in length, and are used one after another to create a much longer streaming experience. As may be appreciated, this format provides a convenient and easy form of streaming as its fairly straight forward programming (after 10 seconds create a new file to write new content to and upload the last file to a server). This may also work well for distribution as it allows GDS providers to cache these files and distribute them to large populations rather than going to get that information from a server. Extracted data may be transcoded 370 to a playback format, for example, MP3. The result is a set of small MP3 files 375 which can be played one after another to produce a longer audio recording. The MP3 files 375 may be automatically transcribed 380 by a computing device into text 385 which may be stored in a schedule table 390 for output to support team members for review at pre-scheduled times.

The information generated by use of the IoT device 110 may be made available to a special needs child's entire support team through for example, computing devices 500. These symptoms and behaviors can be monitored by each part of the child's support team for adjustments in treatment or support behaviors in order to more accurately adjust to the special needs student's unique needs. In some embodiments, an online platform is provided that tracks and displays the information generated by the IoT device 110 use. Parents, teachers, therapists and doctors can sign up to the platform to analyze both behavior and symptom events or changes in the pattern of those behavior and symptom events.

The child's support team can leverage a mobile app or website to access the child's information. The support team can then add context-based information to the information, such as activities, schedules or observations which provide better context as to the atmosphere or other contributors to the child's symptoms or behaviors. The support team's information can also provide access to other/new support team members. This information may also be stored in a database, which will be used for providing access rights to the child's data.

As will be appreciated, aspects of the above disclosed technology improve on the current technologies for assisting special needs children. Data being tracked, stored, analyzed by machine learning and automatically generating a prognosis via a dedicated device provides support team members a better and more reliable record of the special needs individual's behaviors and symptoms. A support team can leverage the scientific method by analyzing organic data supplied by the individual and verify theories on the individual's support needs, increasing the quality of care received. In addition, efficiency is increased by reducing time spent by the support team generating paper reports. Still yet, information is maintained more securely and becomes less susceptible to mistaken disclosures to individuals who should not have access to the information because the information is held in a secure, remote server or cloud-based network.

Figure 6:
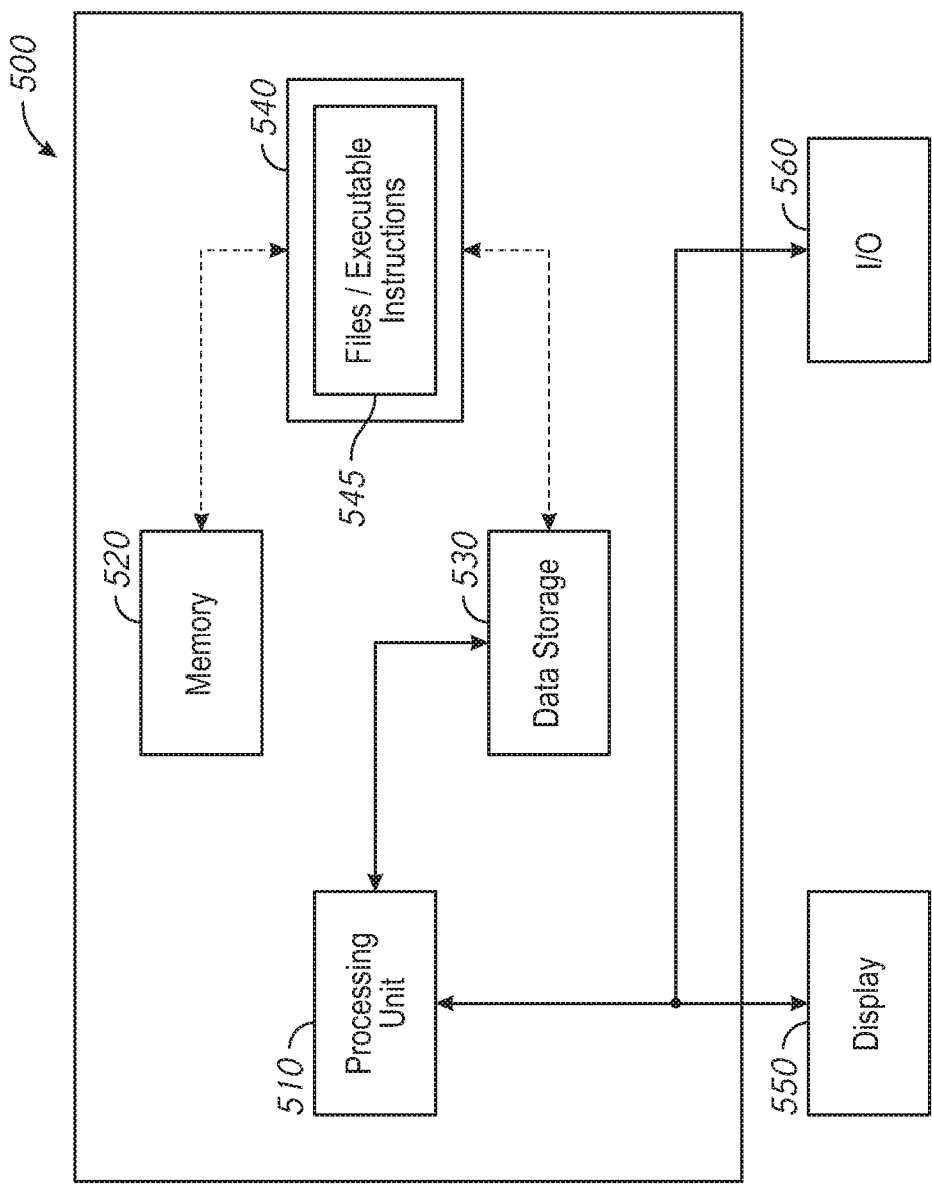
FIG. 6 is a block diagram of a computing device for use in embodiments of the subject technology.

Referring now to FIG. 6, a computing device 500 is shown in detail according to an exemplary embodiment. The computing device 500 may be for example, a computer system or a computer server. While the end devices in FIG.

4 are labeled as computing devices 500, other elements in FIGS. 4 and 5 may also be computing devices under this description (for example, the phone/computer 120, any of the computing devices of IoT service endpoint 145, the processing server 150, as well as one or more elements in combination on the right side of FIG. 5 may be a part of or included within a computing device 500). As will be appreciated, some aspects of the embodiments disclosed above may turn the computing device 500 into a special purpose computer system. For example, in the role of the processing server 150, a computing device 500 may analyze the received data and determine what behaviors match the pattern or verbal cue received. In addition, the computing device 500 may identify deviations in patterns and determine when the deviations signal some other symptom (for example, within a machine learning context). Furthermore, the computing device 500 may be configured to specifically determine prognoses based on the information received and comparisons to data on record. In the role of a user device, the computing device 500 is generally not a server but may instead be desktop computers, tablet or laptop computers, all-in-one computer stations, a mobile computing device (for example, a smart phone, smart wearable devices (glasses, jewelry, watches, ear wear, etc.), or programmable electronics.

The components of the computer system or server, may include, but are not limited to, one or more processors or processing units 510, a system memory 520, data storage 530 (sometimes referred to as memory or memory storage), a computer program product 540 having a set of program modules 545 including files and executable instructions, and a bus system that couples various system components including the system memory 520 to the processor(s) 510. The system memory 520 may store for example, electronic files of the image objects to be printed.

In some embodiments, the processors 510 are dedicated computer processors which implement the processes described above, including for example, machine learning processes related to comparisons, determinations of behavior and deviations from behavior, and automated prognoses.

The computing device 500 may be described in the general context of computer system executable instructions, such as the program modules 545 which represent a software embodiment of the system and processes described generally above. The program modules 545 generally carry out the functions and/or methodologies of embodiments as described above. The computing device 500 may typically include a variety of computer system readable media. Such media could be chosen from any available media that is accessible by the computing device 500, including non-transitory, volatile and non-volatile media, removable and non-removable media for use by or in connection with an instruction execution system, apparatus, or device. A computer readable storage medium may be, for example, but not limited to, an electronic, magnetic, optical, electromagnetic, infrared, or semiconductor system, apparatus, or device, or any suitable combination of the foregoing. The system memory 520 could include one or more computer system readable media in the form of volatile memory, such as a random-access memory (RAM) and/or a cache memory. By way of example only, the data storage system 530 may read from and write to a non-removable, non-volatile magnetic media device. The system memory 520 may include at least one program product 540 having a set of program modules 545 that are configured to carry out the functions of embodiments of the invention in the form of computer executable instructions. The program product/utility 540, having a set of program modules 545, may be stored in the system memory 520 by way of example, and not limitation, as an operating system, one or more application programs, other program modules, and program data. Some embodiments may generate an electronic user interface (viewable and controllable from a display 550) that may allow the user to enter image objects for processing.

The computing device 500 may communicate with one or more external devices including for example, an electronic display 550 which may in some embodiments be configured for tactile response as in a touch screen display. User input into the display 550 may be registered at the processor 510 and processed accordingly. Other devices may enable the computing device 500 to communicate with one or more other computing devices, either by hardwire or wirelessly. Such communication can occur via Input/Output (I/O) interfaces/ports 560. In some embodiments, the I/O interfaces/ports 560 may be specially configured to handle aspects of the embodiments described herein converting the computing device 500 into a special purpose machine. For example, as a processing point, the I/O interfaces/ports 560 may be configured to transmit receipt of the button press data patterns in signal formats specifically for implementation in analyzing patterns for generating a prognoses for a special needs individual.

The computing device 500, through the I/O interface/ports 560, may communicate with one or more networks such as a local area network (LAN), a general wide area network (WAN), and/or a public network (e.g., the Internet) via a network adapter as is commonly known in the art. Each of the operating system, one or more application programs, other program modules, and program data or some combination thereof, may include an implementation of a networking environment. In some embodiments, the computing device 500 may be a cloud computing node connected to a cloud computing network (not shown). The computer computing device 500 may be practiced in distributed cloud computing environments where tasks are performed by remote processing devices that are linked through a communications network. In a distributed cloud computing environment, program modules may be located in both local and remote computer system storage media including memory storage devices. Support team members may contribute behavioral data from different locations or times to the system 100 in a cloud-based network.

As will be appreciated by one skilled in the art, aspects of the disclosed invention may be embodied as a system, method or process, or computer program product. Accordingly, aspects of the disclosed invention may take the form of an entirely hardware embodiment, an entirely software embodiment (including firmware, resident software, microcode, etc.) or an embodiment combining software and hardware aspects that may all generally be referred to herein as a "module", "circuit", or "system." For example, a "memory module" may in some hardware embodiments be any one of the system memory 520, the data storage 530 or any combination thereof. Furthermore, aspects of the disclosed invention may take the form of a computer program product embodied in one or more computer readable media having computer readable program code embodied thereon.

Aspects of the disclosed invention are described above with reference to block diagrams of methods, apparatus (systems) and computer program products according to embodiments of the invention. It will be understood that each block of the block diagrams, and combinations of blocks in the flowchart illustrations and/or block diagrams, can be implemented by computer program instructions.

These computer program instructions may be provided to the processor 510 of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks in the figures.

Those of skill in the art would appreciate that various components and blocks may be arranged differently (e.g., arranged in a different order, or partitioned in a different way) all without departing from the scope of the subject technology. The previous description is provided to enable any person skilled in the art to practice the various aspects described herein. The previous description provides various examples of the subject technology, and the subject technology is not limited to these examples. Various modifications to these aspects will be readily apparent to those skilled in the art, and the generic principles defined herein may be applied to other aspects.

Thus, the claims are not intended to be limited to the aspects shown herein, but are to be accorded the full scope consistent with the language of claims, wherein reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

The word "exemplary" is used herein to mean "serving as an example or illustration." Any aspect or design described herein as "exemplary" is not necessarily to be construed as preferred or advantageous over other aspects or designs.

Moreover, nothing disclosed herein is intended to be dedicated to the public regardless of whether such disclosure is explicitly recited in the claims. No claim element is to be construed under the provisions of 35 U.S.C. @ 112, sixth paragraph, unless the element is expressly recited using the phrase "means for" or, in the case of a method claim, the element is recited using the phrase "step for." Furthermore, to the extent that the term "include," "have," or the like is used in the description or the claims, such term is intended to be inclusive in a manner similar to the term "comprise" as "comprise" is interpreted when employed as a transitional word in a claim.

What is claimed is:

1. A system for automated behavioral analysis of a special needs individual, comprising:
    an Internet of Things (IoT) device including,
        one or more buttons,
        a temporary memory storage in the IoT device for recording and storing button presses from a user, and
        a wireless module configured to transmit recorded button press signals; and
    a host server or cloud-based server network, including a processing unit configured to:
        receive the transmitted recorded button press signals;
        operate a processing server configured to analyze the transmitted recorded button press signals for patterns, wherein different patterns of button press signals are associated with different behaviors of the special needs individual and the different behaviors and their respective associated patterns of button press signals are stored in a file of the special needs individual;
        retrieve a list of behaviors associated with the special needs individual from the stored files;
        identify behaviors associated with the recorded button press signals based on retrieved list of behaviors; and
        generate an automated prognosis of the identified behaviors, wherein the automated prognosis is output into an electronically displayed result.

2. The system of claim 1, further comprising an automated alert system including an SMS text system, a push notification system and an electronic mail module, wherein the processing unit is further configured to send the electronically displayed result to a support team member through one or more of the SMS text system, the push notification system, and the electronic mail module.

3. The system of claim 1, further comprising a unique electronic identifier for the IoT device, stored in the IoT device, wherein the unique identifier of the IoT device is associated with the special needs individual.

* * * * *